United States Patent
Iversen et al.

Patent Number: 6,045,553
Date of Patent: Apr. 4, 2000

[54] HYBRID SKULL PINS

[75] Inventors: Alfred A. Iversen, Wayzata; Eric F. Caillé, Richfield, both of Minn.

[73] Assignee: PMT Corporation, Chanhassen, Minn.

[21] Appl. No.: 09/170,267

[22] Filed: Oct. 13, 1998

[51] Int. Cl.⁷ .................................................. A61B 17/24
[52] U.S. Cl. .................................. 606/61; 606/72; 606/75
[58] Field of Search ................................ 606/72, 73, 75, 606/61, 60, 130, 76; 602/16, 18, 37

[56] References Cited

U.S. PATENT DOCUMENTS

| | | | |
|---|---|---|---|
| D. 313,471 | 1/1991 | Bremer . | |
| 4,476,590 | 10/1984 | Scales et al. | 606/76 |
| 4,612,930 | 9/1986 | Bremer . | |
| 5,042,462 | 8/1991 | Bremer . | |
| 5,122,132 | 6/1992 | Bremer . | |
| 5,347,894 | 9/1994 | Fischer . | |
| 5,360,448 | 11/1994 | Thramann | 623/16 |
| 5,505,736 | 4/1996 | Reimels et al. | 606/72 |

*Primary Examiner*—Michael Buiz
*Assistant Examiner*—Lien Ngo
*Attorney, Agent, or Firm*—Anthony G. Eggink

[57] ABSTRACT

A hybrid skull pin to adjust and hold a cervical fixation device to the skull of a patient. The hybrid skull pin is constructed of at least two different materials and arranged to permit cervical fixation devices to be used in MRI procedures. The hybrid skull pin has an elongated body with exterior threads and a tip portion for engaging the skull of the patient. A nonconductive coating extends over the tip portion of the skull pin body. The hybrid skull pin further includes an insert secured in the elongated body. The insert is constructed of a second material and secured in a cavity of the pin. The insert reduces the mass of the skull pin thereby reducing or eliminating the radio frequency energy conducted through the pin during MRI procedures. The insert also acts as a heat capacitor which absorbs the radio frequency energy and the magnetic field vibrations generated in the MRI environment. By preventing a "heat sensation" conducted to the patient's skin, the use of the hybrid skull pin structure reduces or eliminates discomfort to the patient while wearing a cervical fixation device in an MRI procedure.

20 Claims, 2 Drawing Sheets

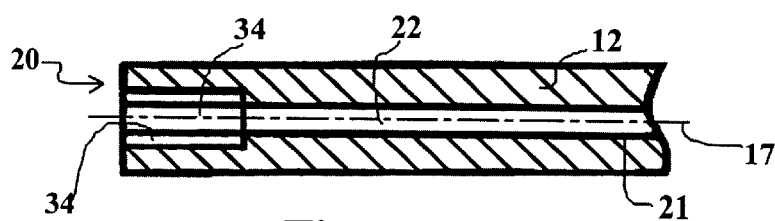
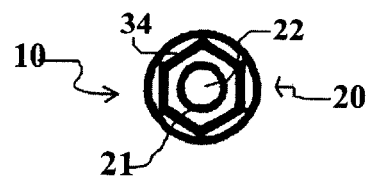
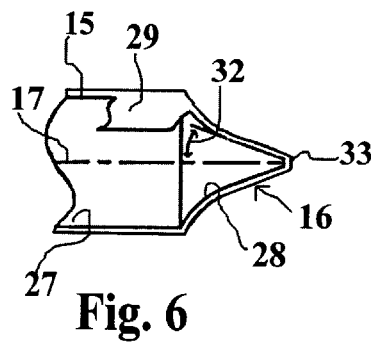

HYBRID SKULL PINS

BACKGROUND OF THE INVENTION

The present invention relates generally to cervical fixation devices and more particularly to an improved screw pin structure that is used in connection with a cervical fixation device. Cervical fixation devices are typically used to immobilize the head and neck of a patient having suffered cervical trauma.

In the field of cervical fixation devices several different types of skull pins have been proposed and used. For example, in U.S. Pat. Nos. 4,612,930, 5,042,462, 5,122,132, and D313,471 to Bremer, and 5,347,894 to Fischer such cervical fixation devices are disclosed. As shown in these patent references, skull pins are used to secure a halo cervical fixation or similar device in a predetermined and aligned manner to a patient's skull.

Some problems and difficulties have been found, however, when a person wearing a cervical fixation device is scanned using a Magnetic Resonance Imaging (MRI) procedure. Magnetic Resonance Imaging is a technique in which an object placed in a spatially varying magnetic field is subjected to a pulse of radio frequency radiation, and the resulting nuclear magnetic resonance spectra are combined to give cross-sectional images. MRI procedure devices may be used on patients wearing cervical fixation devices to monitor the healing development of the trauma in the patient's body.

The skull pins used in the prior art cervical fixation devices have been found to act like an antenna, receiving the ambient radio frequency energy generated by the MRI. The prior art skull pin structures have been found to act as a vehicle for the conduction of radio frequency energy generated by the MRI to the patient's skin, which in effect, acts as a ground for the antenna. This phenomenon creates a sensation of heating of the skull pin at the point of contact with the patient's skin. In addition, the vibrations caused by the magnetic field generated by the MRI are transmitted through the skull pins to the patient's skin also creating a heating sensation. Prior art skull pins are typically constructed of a conductive metallic composition conducive to electrical and thermal transfer.

In summary, the phenomenon of heating of the skull pin by the above sources causes discomfort to the patient and raise issues of patient safety and comfort when wearing a cervical fixation device in an MRI procedure. Furthermore, the skull pins developed to solve this problem have been constructed with either a ceramic tip or an entire ceramic body. The ceramic material has been found to be prone to breakage because of its inherently brittle composition.

The hybrid skull pins of the present invention are provided to alleviate these problems. The term hybrid skull pin, for the purpose of this application, means a skull pin having two or more different compositions or types of structures in its embodiment.

The hybrid skull pin of the present invention is constructed of a hybrid material composition and is provided with at least a nonconductive tip that reduces or eliminates the "grounding effect" and which has the structural integrity to secure a cervical fixation device when engaged with the skull of the patient.

SUMMARY OF THE INVENTION

This invention relates to a hybrid skull pin constructed and arranged for use in cervical fixation devices. The skull pin is constructed of a hybrid material to reduce or eliminate the transfer of energy and vibration resulting from wearing a cervical fixation device while being scanned in an MRI procedure. The hybrid skull pin is comprised of a generally cylindrical body having an outer surface, a first end, a second end, and a central axis. The first end of the body is constructed and arranged to form a tip portion for engaging the skull of a patient. A nonconducive material is coated on at least the tip portion of the skull pin body. The skull pin body has a cavity which extends generally along the central axis and which extends from the second end a predetermined depth into the cylindrical body. A ceramic insert is secured in the cavity by either a frictional press insertion or by adhesive bonding inside the cavity of the cylindrical body.

The nonconductive coating and ceramic insert may be used separately or in combination with each other to form the hybrid skull pins of this invention. The nonconductive coating and ceramic insert, when combined, reduce the mass of the skull pin to thereby reduce or eliminate the radio frequency conducted through the pin when the cervical fixation device is worn during an MRI procedure. The ceramic insert itself acts as a heat capacitor which absorbs the radio frequency and the magnetic field vibrations generated in the MRI environment. The nonconductive coating, such as a nonconductive polymer material, further reduces a "heat sensation" conducted to the patient's skin. The use of the hybrid skull pin structure of this invention reduces or eliminates discomfort to the patient while wearing a cervical fixation device in an MRI procedure.

These and other benefits of this invention will become clear from the following description, by reference to the drawings.

BRIEF DESCRIPTION OF THE DRAWINGS

FIG. 4 is an enlarged cut-away side view showing the elongated body of the skull pin of FIG. 2;

FIG. 5 is an enlarged rear plan view of the hybrid skull pin of FIG. 2 and showing the ceramic insert position therein; and FIG. 6 is an enlarged cut-away side view of the tip portion of the hybrid skull pin of FIG. 2 and showing the nonconductive coating applied thereon.

DESCRIPTION OF THE PREFERRED EMBODIMENTS

Figure 1:
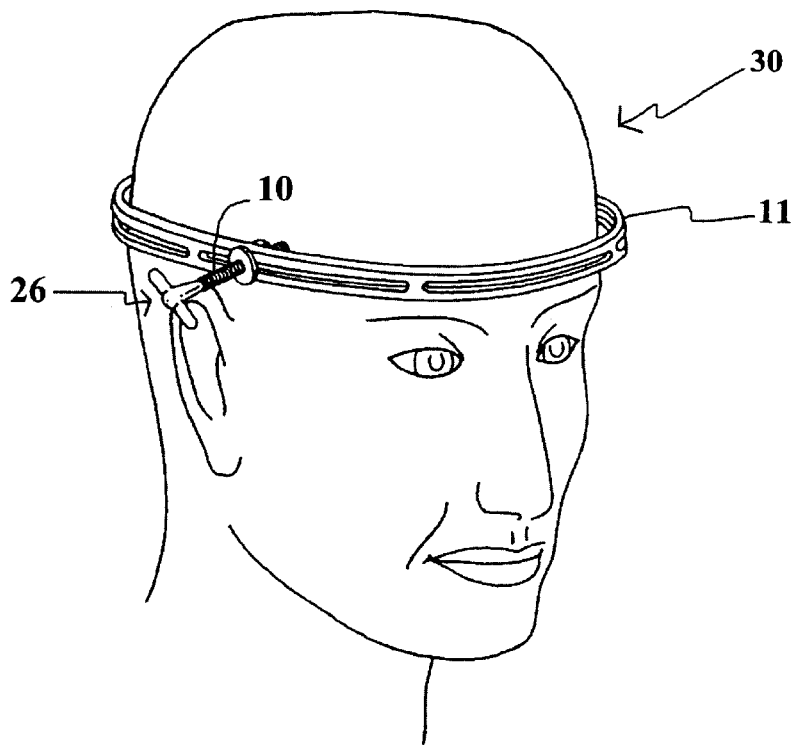
FIG. 1 is a perspective view of a patient's head equipped with a cervical fixation device and shown using a hybrid skull pin of the present invention in conjunction with a torque limiting device.

Referring to FIG. 1, the hybrid skull screw pin 10 of the present invention is constructed and arranged to be used in a cervical fixation device 11. As shown, a halo cervical fixation device 11 is secured in an aligned manner to the skull 30 of a patient. The skull screw pins 10 are used as part of the cervical fixation device 11 to immobilize the head and neck of the patient having suffered cervical trauma, for example. The torque-limiting device 26 shown in FIG. 1 is disclosed in Fischer, U.S. Pat. No. 5,347,894, assigned to Applicants' assignee, and is incorporated by reference herein.

Referring to drawing FIGS. 2–6, the hybrid skull pin of the present invention is indicated generally as numeral 10.

The skull pin 10 is shown comprised of a skull pin body 12 having a first end 14 and a second end 20. The first end 14 of the skull pin body 12 is comprised of a head portion 15 having a tip portion 16. The skull pin 10 is constructed of a hybrid material to reduce or eliminate the transfer of energy and vibration through the skull pin structure.

Figure 2:
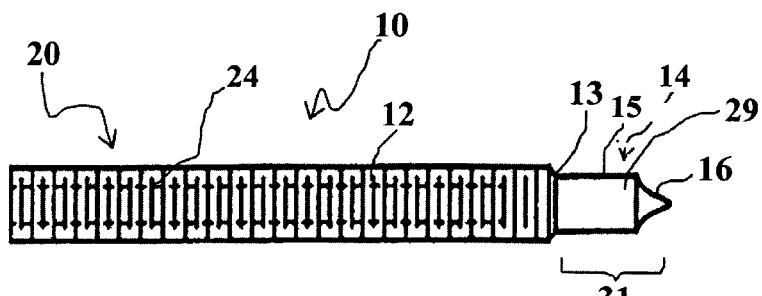
FIG. 2 is a lateral plan view of a hybrid skull pin of the present invention.

In the preferred embodiment shown in FIG. 2, the skull pin body 12 is shown to have a larger diameter than the diameter of the head portion 15 and tip portion 16. A sloped transitional area 13 smoothes the transition between the head portion 15 and the remainder of the skull pin body 12.

As further shown in FIGS. 4 and 5, the cavity 21 extends axially from the second end 20 into the body 12 of the skull pin 10. It is preferred that the ceramic insert 22 is fixed in the cavity 21 beginning at the end of the hexagonal cavity 34 and extending toward the head portion 15. It is preferred that the cavity 21 extend at least to the head portion 15, however, the cavity and insert may extend into the head portion 15 itself. The ceramic insert 22 is preferably at least 2 inches in length.

As shown in FIG. 2, the hybrid skull screw pin 10 has a cylindrical body 12 that typically may have a length of approximately 3 inches as measured from the tip portion 16 to the second end 20. The body 12 typically has a diameter of approximately 0.25 inches. The slotted cavity 34 dimension for this size skull pin 10 is preferably a 0.188 ANSI Standard #4 Hex. (hexagonal cavity).

Figure 3:
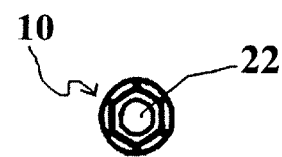
FIG. 3 is a rear plan view of the hybrid skull pin of FIG. 2 and showing the ceramic insert positioned therein.

As shown in FIG. 3, the second end 20 of the skull screw pin 10 has a cavity 21 extending along its central axis 17 of the skull pin body 12. The cavity 21 is aligned along the central axis 17 of the skull pin 10. A ceramic insert 22 is shown positioned within cavity 21. The cavity entrance has a slotted cavity portion 34 in the second end 20 which allows for the use of a torque-limiting device 26, the latter being shown used in FIG. 1.

The skull pin body 12 is preferably constructed, for example, of a 6AI-4V ELI Titanium material or the like. The exterior surface 23 of the cylindrical body 12 has a threaded main body portion 24 that comprises approximately 85% of the overall length of the pin body 12. The remainder of the pin body preferably consists of a cylindrical head portion 15 having a conical tip portion 16 shown at first end 14. As shown in FIG. 2, the skull screw body 12 has a threaded portion 24 on its periphery. The threads are adapted to be screwed into the internally threaded apertures of the cervical fixation device 11.

The body 12 of the hybrid skull pin 10 is shown coated with a nonconductive layer 29 on the exterior surface 28 of the tip portion 16 of the screw pin 10 and the exterior surface 27 of the head portion 15, to act as a separation or insulation layer between the patient's skin and the skull pin body 12. FIG. 2 shows the nonconductive coating to extend over the head portion 15 as indicated by 31. As will be further discussed, the nonconductive layer 29 may extend beyond the head portion 15 and over the rearward portions of the skull screw body 12, for example, onto the threaded portion. The nonconductive material or insulation layer 29 reduces or eliminates the conduction of radio frequency energy by removing the grounding effect to the patient's skin. In the preferred embodiment, the nonconductive coating is preferably between 0.002 and 0.050 inches in thickness. The nonconductive coating on the skull pin tips 16 is preferably biocompatible, MRI Compatible and CT Transparent. For example, various nonconductive polymer materials having these qualities may be utilized. Thus, the nonconductive coating material for the pin body 12 may be a nonconductive polymer and, alternatively, a ceramic coating may be used for providing the nonconductive layer of the invention. It is preferred that the nonconductive layer 29 be bonded to at least the head portion 15 of the hybrid skull screw pin 10, as shown in FIG. 6. The layer 29 may also be coated over other portions of the skull screw body 12. For example, the nonconductive layer 29 may extend over the entire screw body 12 including over the exterior threads 24 of the second end 20. This nonconductive layer 29 will further provide an insulative layer between the skull pin 10 and the skull 30 of the patient.

As shown in FIG. 4, another embodiment of the hybrid skull pin 10 includes the insertion of a second predetermined material into the core of the pin body 12. For example, introduction of a ceramic insert 22 into the core or cavity 21 of the pin body 12 reduces the metallic mass of the skull pin 10 and acts as a heat capacitor. By reducing the mass of the skull pin 10, the radio frequency energy transferred to the patient's skin is reduced or eliminated. The ceramic insert 22 also acts as a heat capacitor which further helps to absorb the heat created from both heat sources, namely, the radio frequency energy and the magnetic field vibrations generated by the MRI field. In addition, the ceramic insert 22 absorbs or eliminates the magnetic field vibration caused by the MRI field. The ceramic material used for the insert 22 is preferably MRI compatible and CT Transparent. The ceramic insert 22 is shown placed in central cavity 21 of the pin body 12. The insert is preferably at least two inches in length and preferably extends to the end of the slotted cavity 34 which is provided to receive a torque limiting device 26. The ceramic insert 22, as shown, may have a diameter of approximately 0.125 inches. The insert 22 has an equal or smaller diameter than the diameter of the cavity 21. The insert 22 is preferably fixed in the cavity, either by a frictional press insertion process or the insert may alternatively be bonded to the titanium body structure utilizing an epoxy or like adhesive.

As particularly shown in FIG. 6, the head portion 15 is cylindrical in configuration and has a conical tip portion 16 extending therefrom. The tip portion 16 slopes toward the tip end to define a point 33 for engaging the skull of the patient. The slope or angle of this conical tip portion configuration is shown as angle 32 which is measured in section with respect to the central axis 17 to be an acute angle of approximately 20 degrees. The tip point 33 is preferably approximately 0.01 inches in diameter.

As many changes are possible to the embodiments of this invention, utilizing the teachings thereof, the description above, and the accompanying drawings should be interpreted in the illustrative, and not in the limited sense.

That which is claimed:

1. A hybrid skull pin for use in a cervical fixation device comprising:

a) a generally cylindrical body having an outer surface, a central axis, a first end, and a second end, said first end comprising of a head portion having a tip portion for engaging the skull of a patient; and b) an insulative, non-porous, non-bone ingrowth promoting and nonconductive polymer material on said outer surface of said tip portion, whereby the nonconductive material permits the use of the cervical fixation device in an MRI procedure.

2. The hybrid skull pin of claim 1, wherein said nonconductive material extends over said head portion of said generally cylindrical body.

3. The hybrid skull pin of claim 2, wherein said nonconductive material is comprised of a polymer and has a thickness between 0.002 and 0.050 inches.

4. The hybrid skull pin of claim 1, wherein said nonconductive material extends over said outer surface of said cylindrical body.

5. The hybrid skull pin of claim 1, wherein said generally cylindrical body is constructed of a titanium composition.

6. The hybrid skull pin of claim 1, wherein said outer surface of said cylindrical body portion is threaded over a substantial portion thereof.

7. The hybrid skull pin of claim 6, wherein said threaded portion is approximately 85% of said cylindrical body.

8. The hybrid skull pin of claim 1, wherein said tip portion is generally conical in shape and having its surface tapering away from said generally cylindrical body at an angle of approximately 20 degrees with respect to said central axis and wherein said tip portion has a point surface for engaging the skull of a patient.

9. The hybrid skull pin of claim 8, wherein said point of said tip portion has a point surface that is generally circular in cross-section and is oriented generally in a plane perpendicular to said central axis, said point surface having a diameter of approximately 0.010 inches.

10. A hybrid skull pin for use in a cervical fixation device used in an MRI procedure comprising:
    a) a generally cylindrical body having an outer surface, a first end, a second end, and a central axis, said first end being constructed and arranged to form a tip portion;
    b) a cavity in said second end of said generally cylindrical body extending along said central axis a predetermined depth; and
    c) a ceramic insert having a cylindrical structure, a predetermined length and being secured in said cavity, whereby the insert permits the use of the cervical fixation device in an MRI procedure.

11. The hybrid skull pin of claim 10, wherein said insert is frictionally secured in said cavity.

12. The hybrid skull pin on claim 10, wherein said insert is secured in said cavity by an adhesive.

13. The hybrid skull pin of claim 12, wherein said adhesive is an epoxy.

14. A hybrid skull pin for use in a cervical fixation device comprising:
    a) a generally cylindrical body having an outer surface, a first end, a second end, and a central axis, said first end comprising a head portion having a tip portion for engaging the skull of a patient;
    b) a nonconductive material coated on at least said outer surface of said tip portion, whereby the nonconductive material permits the use of the cervical fixation device in an MRI procedure;
    c) a cavity in said second end of said generally cylindrical body and extending along said central axis a predetermined depth; and
    d) a ceramic insert having a cylindrical structure, a predetermined length and being secured in said cavity, whereby the insert permits the use of the cervical fixation device in an MRI procedure.

15. The hybrid skull pin of claim 14, wherein said ceramic insert extends in said cavity to at least said head portion.

16. The hybrid skull pin of claim 14, wherein said second end of said cylindrical body has a tool engaging slot, whereby said hybrid skull screw pin is adapted to receive a torque limiting tool.

17. The hybrid skull pin of claim 16, wherein said slot is hexagonal in shape.

18. The hybrid skull pin of claim 14, wherein said generally cylindrical body is comprised of a titanium material.

19. The hybrid skull pin of claim 14, wherein said ceramic insert is comprised of Alumina AD-998, ZTA or like ceramic material.

20. The hybrid skull pin of claim 14 wherein said nonconductive material is comprised of a polymer and has a thickness between 0.002 and 0.050 inches.

* * * * *